(12) United States Patent
Jacobson

(10) Patent No.: US 8,010,209 B2
(45) Date of Patent: Aug. 30, 2011

(54) DELIVERY SYSTEM FOR IMPLANTABLE BIOSTIMULATOR

(75) Inventor: Peter M. Jacobson, Chanhassen, MN (US)

(73) Assignee: Nanostim, Inc., Milpitas, CA (US)

( * ) Notice: Subject to any disclaimer, the term of this patent is extended or adjusted under 35 U.S.C. 154(b) by 945 days.

(21) Appl. No.: 11/549,574

(22) Filed: Oct. 13, 2006

(65) Prior Publication Data

US 2007/0088418 A1    Apr. 19, 2007

Related U.S. Application Data

(60) Provisional application No. 60/761,531, filed on Jan. 24, 2006, provisional application No. 60/761,740, filed on Jan. 24, 2006, provisional application No. 60/749,017, filed on Dec. 10, 2005, provisional application No. 60/739,901, filed on Nov. 26, 2005, provisional application No. 60/737,296, filed on Nov. 16, 2005, provisional application No. 60/729,671, filed on Oct. 24, 2005, provisional application No. 60/726,706, filed on Oct. 14, 2005.

(51) Int. Cl.
    *A61N 1/372* (2006.01)
(52) U.S. Cl. ....................................................... 607/119
(58) Field of Classification Search ................ 607/9, 27, 607/32, 119, 122; 600/373, 374
    See application file for complete search history.

(56) References Cited

U.S. PATENT DOCUMENTS

| | | |
|---|---|---|
| 3,199,508 A | 8/1965 | Roth |
| 3,212,496 A | 10/1965 | Preston |
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,943,936 A * | 3/1976 | Rasor et al. ........... 607/35 |

(Continued)

FOREIGN PATENT DOCUMENTS

EP    1741465 A1    1/2007

(Continued)

OTHER PUBLICATIONS

PCT International Search Report dated Apr. 8, 2008.

(Continued)

*Primary Examiner* — Niketa I Patel
*Assistant Examiner* — Hiba El-Kaissi
(74) *Attorney, Agent, or Firm* — Shay Glenn LLP

(57) ABSTRACT

A delivery system for implanting a biostimulation device comprising a stylet extending along an axis from knob end to a threaded end configured to engage an internally threaded nut of the biostimulation device and a catheter tube configured to axially contain the stylet. The catheter tube comprises a feature that engages a corresponding feature on the biostimulation device whereby the stylet can be rotated relative to the catheter tube for disengagement of the stylet threaded end from the biostimulation device threaded end.

7 Claims, 12 Drawing Sheets

U.S. PATENT DOCUMENTS

| | | |
|---|---|---|
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A * | 9/1982 | Dutcher et al. ............... 607/119 |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A * | 11/1985 | Schiff ............................ 600/18 |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A * | 12/1989 | Strandberg ...................... 607/18 |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,987,897 A | 1/1991 | Funke |
| 5,010,887 A | 4/1991 | Thornander |
| 5,012,806 A | 5/1991 | De Bellis |
| 5,014,700 A | 5/1991 | Alt |
| 5,014,701 A | 5/1991 | Pless et al. |
| 5,031,615 A | 7/1991 | Alt |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A * | 11/1993 | Bens ............................. 607/127 |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,324,316 A | 6/1994 | Schulman et al. |
| 5,331,966 A | 7/1994 | Bennett et al. |
| 5,333,095 A | 7/1994 | Stevenson et al. |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A * | 5/1995 | Fujii et al. ....................... 607/32 |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,539,775 A | 7/1996 | Tuttle et al. |
| 5,549,654 A | 8/1996 | Powell |
| 5,549,659 A | 8/1996 | Johansen et al. |
| 5,551,427 A * | 9/1996 | Altman ........................ 600/374 |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras |
| 5,598,848 A | 2/1997 | Swanson et al. |
| 5,649,952 A | 7/1997 | Lam |

| | | | |
|---|---|---|---|
| 5,650,759 A | 7/1997 | Hittman et al. | |
| 5,654,984 A | 8/1997 | Hershbarger et al. | |
| 5,662,689 A | 9/1997 | Elsberry et al. | |
| 5,669,391 A | 9/1997 | Williams | |
| 5,674,259 A | 10/1997 | Gray | |
| 5,676,153 A | 10/1997 | Smith et al. | |
| 5,693,076 A | 12/1997 | Kaemmerer | |
| 5,694,940 A | 12/1997 | Unger et al. | |
| 5,694,952 A | 12/1997 | Lidman et al. | |
| 5,697,958 A | 12/1997 | Paul et al. | |
| 5,702,427 A | 12/1997 | Ecker et al. | |
| 5,725,559 A | 3/1998 | Alt et al. | |
| 5,728,154 A | 3/1998 | Crossett et al. | |
| 5,730,143 A | 3/1998 | Schwarzberg | |
| 5,735,880 A | 4/1998 | Prutchi et al. | |
| 5,738,102 A | 4/1998 | Lemelson | |
| 5,740,811 A | 4/1998 | Hedberg et al. | |
| 5,741,314 A | 4/1998 | Daly et al. | |
| 5,766,231 A | 6/1998 | Erickson et al. | |
| 5,792,205 A | 8/1998 | Alt et al. | |
| 5,810,735 A | 9/1998 | Halperin et al. | |
| 5,814,076 A | 9/1998 | Brownlee | |
| 5,814,087 A | 9/1998 | Renirie | |
| 5,814,089 A * | 9/1998 | Stokes et al. | 607/32 |
| 5,824,016 A | 10/1998 | Ekwall | |
| 5,871,451 A | 2/1999 | Unger et al. | |
| 5,876,353 A | 3/1999 | Riff | |
| 5,876,425 A | 3/1999 | Gord et al. | |
| 5,891,178 A | 4/1999 | Mann et al. | |
| 5,899,928 A | 5/1999 | Sholder et al. | |
| 5,935,079 A | 8/1999 | Swanson et al. | |
| 5,954,761 A | 9/1999 | Machek et al. | |
| 5,957,861 A | 9/1999 | Combs et al. | |
| 5,984,861 A | 11/1999 | Crowley | |
| 5,987,352 A | 11/1999 | Klein et al. | |
| 5,995,876 A * | 11/1999 | Kruse et al. | 607/123 |
| 5,999,857 A | 12/1999 | Weijand et al. | |
| 6,002,969 A * | 12/1999 | Machek et al. | 607/122 |
| 6,004,269 A * | 12/1999 | Crowley et al. | 600/439 |
| 6,061,596 A | 5/2000 | Richmond et al. | |
| 6,080,187 A | 6/2000 | Alt et al. | |
| 6,093,146 A | 7/2000 | Filangeri | |
| 6,096,065 A | 8/2000 | Crowley | |
| 6,102,874 A | 8/2000 | Stone et al. | |
| 6,112,116 A | 8/2000 | Fischell et al. | |
| 6,115,628 A | 9/2000 | Stadler et al. | |
| 6,115,630 A | 9/2000 | Stadler et al. | |
| 6,115,636 A | 9/2000 | Ryan | |
| 6,119,031 A | 9/2000 | Crowley | |
| 6,125,290 A | 9/2000 | Miesel | |
| 6,125,291 A | 9/2000 | Miesel et al. | |
| 6,128,526 A | 10/2000 | Stadler et al. | |
| 6,129,751 A * | 10/2000 | Lucchesi et al. | 607/127 |
| 6,132,390 A * | 10/2000 | Cookston et al. | 600/585 |
| 6,132,456 A * | 10/2000 | Sommer et al. | 607/127 |
| 6,134,459 A | 10/2000 | Roberts et al. | |
| 6,134,470 A | 10/2000 | Hartlaub | |
| 6,141,584 A | 10/2000 | Rockwell et al. | |
| 6,141,588 A | 10/2000 | Cox et al. | |
| 6,141,592 A | 10/2000 | Pauly | |
| 6,144,866 A | 11/2000 | Miesel et al. | |
| 6,148,230 A | 11/2000 | KenKnight | |
| 6,152,882 A | 11/2000 | Prutchi | |
| 6,163,723 A | 12/2000 | Roberts et al. | |
| 6,164,284 A | 12/2000 | Schulman et al. | |
| 6,167,310 A | 12/2000 | Grevious | |
| 6,178,349 B1 | 1/2001 | Kieval | |
| 6,178,356 B1 | 1/2001 | Chastain et al. | |
| 6,185,443 B1 | 2/2001 | Crowley | |
| 6,185,452 B1 | 2/2001 | Schulman et al. | |
| 6,185,464 B1 * | 2/2001 | Bonner et al. | 607/119 |
| 6,190,324 B1 | 2/2001 | Kieval et al. | |
| 6,198,952 B1 | 3/2001 | Miesel | |
| 6,201,993 B1 | 3/2001 | Kruse et al. | |
| 6,208,894 B1 | 3/2001 | Schulman et al. | |
| 6,208,900 B1 | 3/2001 | Ecker et al. | |
| 6,223,081 B1 | 4/2001 | Kerver | |
| 6,230,059 B1 | 5/2001 | Duffin | |
| 6,236,882 B1 | 5/2001 | Lee et al. | |
| 6,240,321 B1 * | 5/2001 | Janke et al. | 607/122 |
| 6,243,608 B1 | 6/2001 | Pauly et al. | |
| 6,248,080 B1 | 6/2001 | Miesel et al. | |
| 6,263,245 B1 | 7/2001 | Snell | |
| 6,265,100 B1 | 7/2001 | Saaski et al. | |
| 6,266,554 B1 | 7/2001 | Hsu et al. | |
| 6,272,379 B1 | 8/2001 | Fischell et al. | |
| 6,280,409 B1 | 8/2001 | Stone et al. | |
| 6,289,229 B1 | 9/2001 | Crowley | |
| 6,306,088 B1 | 10/2001 | Krausman et al. | |
| 6,310,960 B1 | 10/2001 | Saaski et al. | |
| 6,315,721 B2 | 11/2001 | Schulman et al. | |
| 6,324,418 B1 | 11/2001 | Crowley et al. | |
| 6,324,421 B1 | 11/2001 | Stadler et al. | |
| RE37,463 E * | 12/2001 | Altman | 600/374 |
| 6,343,227 B1 | 1/2002 | Crowley | |
| 6,343,233 B1 * | 1/2002 | Werner et al. | 607/119 |
| 6,347,245 B1 | 2/2002 | Lee et al. | |
| 6,358,202 B1 | 3/2002 | Arent | |
| 6,361,522 B1 | 3/2002 | Scheiner et al. | |
| 6,363,282 B1 | 3/2002 | Nichols et al. | |
| 6,364,831 B1 | 4/2002 | Crowley | |
| 6,381,492 B1 | 4/2002 | Rockwell et al. | |
| 6,381,493 B1 | 4/2002 | Stadler et al. | |
| 6,381,494 B1 | 4/2002 | Gilkerson et al. | |
| 6,383,209 B1 | 5/2002 | Crowley | |
| 6,385,593 B2 | 5/2002 | Linberg | |
| 6,386,882 B1 | 5/2002 | Linberg | |
| 6,397,100 B2 | 5/2002 | Stadler et al. | |
| 6,402,689 B1 | 6/2002 | Scarantino et al. | |
| 6,405,073 B1 | 6/2002 | Crowley et al. | |
| 6,405,083 B1 | 6/2002 | Rockwell et al. | |
| 6,409,674 B1 | 6/2002 | Brockway et al. | |
| 6,409,675 B1 | 6/2002 | Turcott | |
| 6,412,490 B1 | 7/2002 | Lee | |
| 6,418,346 B1 | 7/2002 | Nelson et al. | |
| 6,423,056 B1 | 7/2002 | Ishikawa et al. | |
| 6,424,866 B2 | 7/2002 | Mika et al. | |
| 6,428,484 B1 | 8/2002 | Battmer et al. | |
| 6,434,429 B1 | 8/2002 | Kraus et al. | |
| 6,438,410 B2 | 8/2002 | Hsu et al. | |
| 6,438,417 B1 | 8/2002 | Rockwell et al. | |
| 6,442,433 B1 | 8/2002 | Linberg | |
| 6,444,970 B1 | 9/2002 | Barbato | |
| 6,445,953 B1 | 9/2002 | Bulkes et al. | |
| 6,458,145 B1 | 10/2002 | Ravenscroft et al. | |
| 6,459,928 B2 | 10/2002 | Mika et al. | |
| 6,459,937 B1 * | 10/2002 | Morgan et al. | 607/126 |
| 6,466,820 B1 | 10/2002 | Juran et al. | |
| 6,468,263 B1 | 10/2002 | Fischell et al. | |
| 6,470,215 B1 | 10/2002 | Kraus et al. | |
| 6,471,645 B1 | 10/2002 | Warkentin et al. | |
| 6,472,991 B1 | 10/2002 | Schulman et al. | |
| 6,477,424 B1 | 11/2002 | Thompson et al. | |
| 6,480,733 B1 | 11/2002 | Turcott | |
| 6,482,154 B1 | 11/2002 | Haubrich et al. | |
| 6,484,055 B1 | 11/2002 | Marcovecchio | |
| 6,484,057 B2 | 11/2002 | Ideker et al. | |
| 6,490,487 B1 | 12/2002 | Kraus et al. | |
| 6,496,715 B1 | 12/2002 | Lee et al. | |
| 6,500,168 B1 | 12/2002 | Jellie | |
| 6,501,983 B1 | 12/2002 | Natarajan et al. | |
| 6,512,949 B1 | 1/2003 | Combs et al. | |
| 6,512,959 B1 * | 1/2003 | Gomperz et al. | 607/122 |
| 6,522,926 B1 | 2/2003 | Kieval et al. | |
| 6,522,928 B2 | 2/2003 | Whitehurst et al. | |
| 6,539,257 B1 | 3/2003 | KenKnight | |
| 6,556,860 B1 | 4/2003 | Groenewegen | |
| 6,558,321 B1 | 5/2003 | Burd et al. | |
| 6,564,807 B1 | 5/2003 | Schulman et al. | |
| 6,567,680 B2 | 5/2003 | Swetlik et al. | |
| 6,571,120 B2 | 5/2003 | Hutten | |
| 6,574,509 B1 | 6/2003 | Kraus et al. | |
| 6,574,511 B2 | 6/2003 | Lee | |
| 6,580,946 B2 | 6/2003 | Struble | |
| 6,580,948 B2 | 6/2003 | Haupert et al. | |
| 6,584,351 B1 | 6/2003 | Ekwall | |
| 6,584,352 B2 | 6/2003 | Combs et al. | |
| 6,589,187 B1 | 7/2003 | Dirnberger et al. | |

| Patent | Date | Name |
|---|---|---|
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2* | 8/2003 | Gomperz et al. ............... 607/7 |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B1 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Reinke et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2* | 8/2004 | Verness ............... 607/122 |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2* | 11/2004 | Rutten et al. ............... 607/122 |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2* | 6/2005 | Denker et al. ............... 607/5 |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2* | 2/2006 | Jenney et al. ............... 607/122 |
| 7,001,372 B2* | 2/2006 | Richter ............... 604/891.1 |
| 7,023,359 B2 | 4/2006 | Goetz et al. |
| 7,146,222 B2* | 12/2006 | Boling ............... 607/116 |
| 7,146,225 B2* | 12/2006 | Guenst et al. ............... 607/119 |
| 7,164,950 B2 | 1/2007 | Kroll et al. |
| 7,181,505 B2 | 2/2007 | Haller et al. |
| 7,187,971 B2* | 3/2007 | Sommer et al. ............... 607/3 |
| 7,200,437 B1 | 4/2007 | Nabutovsky et al. |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,630,767 B2 | 12/2009 | Poore et al. |
| 7,634,313 B1 | 12/2009 | Kroll et al. |
| 2002/0099430 A1* | 7/2002 | Verness ............... 607/122 |
| 2002/0116028 A1 | 8/2002 | Greatbatch et al. |
| 2002/0147488 A1* | 10/2002 | Doan et al. ............... 607/122 |
| 2003/0040666 A1* | 2/2003 | Rutten et al. ............... 600/374 |
| 2003/0163184 A1 | 8/2003 | Scheiner |
| 2004/0011366 A1 | 1/2004 | Schulman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1* | 9/2004 | Seifert et al. ............... 607/119 |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1* | 12/2005 | Marnfeldt et al. ............... 607/116 |
| 2005/0288722 A1* | 12/2005 | Eigler et al. ............... 607/9 |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1* | 11/2006 | Seifert et al. ............... 607/122 |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088400 A1 | 4/2007 | Jacobson |
| 2007/0088405 A1 | 4/2007 | Jacobson |
| 2007/0276004 A1 | 11/2007 | Hirsch et al. |
| 2007/0293904 A1 | 12/2007 | Gelbart et al. |
| 2008/0004535 A1 | 1/2008 | Smits |
| 2008/0119911 A1 | 5/2008 | Rosero |
| 2008/0269591 A1 | 10/2008 | Halperin et al. |
| 2009/0082828 A1 | 3/2009 | Ostroff |
| 2009/0171408 A1 | 7/2009 | Solem |

FOREIGN PATENT DOCUMENTS

| | | |
|---|---|---|
| WO | WO 98/37926 A1 | 9/1998 |
| WO | WO 2006/065394 A1 | 6/2006 |
| WO | WO 2007/047681 A2 | 4/2007 |
| WO | WO 2007/059386 A2 | 5/2007 |

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. No. 7,630,767).

Beeby et al.; Micromachined silicon generator for harvesting power from vibrations; (Proceedings) PowerMEMS 2004; Kyoto, Japan; pp. 104-107; Nov. 28-30, 2004.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; 2005.

Lüchinger ; Safety aspects of cardiac pacemakers in magnetic resonance imaging; Dissertation submitted to the Swiss Federal Institute of Technology Zurich; 2002.

Nyenhuis et al.; MRI and Implanted Medical Devices: Basic Interactions with an emphasis on heating; vol. 5; No. 3; pp. 467-480; Sep. 2005.

Ostroff, Alan; U.S. Appl. No. 12/568,513 entitled "MRI Compatible Leadless Cardiac Pacemaker," Sep. 28, 2009.

Ostroff, Alan; U.S. Appl. No. 12/698,969 entitled "Leadless Cardiac Pacemaker with Secondary Fixation Capability," filed Feb. 2, 2010.

Shellock et al.; Cardiac pacemaker: In vitro assessment at 1.5 T; Am Heart J; vol. 151; pp. 436-443; 2006.

* cited by examiner

DELIVERY SYSTEM FOR IMPLANTABLE BIOSTIMULATOR

CROSS REFERENCE TO RELATED APPLICATIONS

This application claims the benefit of priority to and incorporates herein by reference in its entirety for all purposes, Provisional U.S. Patent Application Nos. 60/726,706 entitled "LEADLESS CARDIAC PACEMAKER WITH CONDUCTED COMMUNICATION," filed Oct. 14, 2005; 60/761,531 entitled "LEADLESS CARDIAC PACEMAKER DELIVERY SYSTEM," filed Jan. 24, 2006; 60/729,671 entitled "LEADLESS CARDIAC PACEMAKER TRIGGERED BY CONDUCTED COMMUNICATION," filed Oct. 24, 2005; 60/737,296 entitled "SYSTEM OF LEADLESS CARDIAC PACEMAKERS WITH CONDUCTED COMMUNICATION," filed Nov. 16, 2005; 60/739,901 entitled "LEADLESS CARDIAC PACEMAKERS WITH CONDUCTED COMMUNICATION FOR USE WITH AN IMPLANTABLE CARDIOVERTER-DEFIBRILLATOR," filed Nov. 26, 2005; 60/749,017 entitled "LEADLESS CARDIAC PACEMAKER WITH CONDUCTED COMMUNICATION AND RATE RESPONSIVE PACING," filed Dec. 10, 2005; and 60/761,740 entitled "PROGRAMMER FOR A SYSTEM OF LEADLESS CARDIAC PACEMAKERS WITH CONDUCTED COMMUNICATION," filed Jan. 24, 2006; all by Peter M. Jacobson.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is usually performed by a pulse generator implanted subcutaneously or sub-muscularly in or near a patient's pectoral region. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Pulse generator parameters are usually interrogated and modified by a programming device outside the body, via a loosely-coupled transformer with one inductance within the body and another outside, or via electromagnetic radiation with one antenna within the body and another outside.

Although more than one hundred thousand conventional cardiac pacing systems are implanted annually, several well-known difficulties exist.

For example, a pulse generator, when located subcutaneously, presents a bulge in the skin that patients can find unsightly or unpleasant. Patients can manipulate or "twiddle" the device. Even without persistent twiddling, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The at least one male connector mates with at least one corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. The complex connection between connectors and leads provides multiple opportunities for malfunction.

For example, failure to introduce the lead pin completely into the terminal block can prevent proper connection between the generator and electrode.

Failure to insert a screwdriver correctly through the setscrew slot, causing damage to the slot and subsequent insulation failure.

Failure to engage the screwdriver correctly in the setscrew can cause damage to the setscrew and preventing proper connection.

Failure to tighten the setscrew adequately also can prevent proper connection between the generator and electrode, however over-tightening of the setscrew can cause damage to the setscrew, terminal block, or lead pin, and prevent disconnection if necessary for maintenance.

Fluid leakage between the lead and generator connector moldings, or at the setscrew cover, can prevent proper electrical isolation.

Insulation or conductor breakage at a mechanical stress concentration point where the lead leaves the generator can also cause failure.

Inadvertent mechanical damage to the attachment of the connector molding to the generator can result in leakage or even detachment of the molding.

Inadvertent mechanical damage to the attachment of the connector molding to the lead body, or of the terminal pin to the lead conductor, can result in leakage, an open-circuit condition, or even detachment of the terminal pin and/or molding.

The lead body can be cut inadvertently during surgery by a tool, or cut after surgery by repeated stress on a ligature used to hold the lead body in position. Repeated movement for hundreds of millions of cardiac cycles can cause lead conductor breakage or insulation damage anywhere along the lead body.

Although leads are available commercially in various lengths, in some conditions excess lead length in a patient exists and is to be managed. Usually the excess lead is coiled near the pulse generator. Repeated abrasion between the lead body and the generator due to lead coiling can result in insulation damage to the lead.

Friction of the lead against the clavicle and the first rib, known as subclavian crush, can result in damage to the lead.

In many applications, for example dual-chamber pacing, multiple leads are implanted in the same patient and sometimes in the same vessel. Abrasion between the leads for hundreds of millions of cardiac cycles can cause insulation breakdown or even conductor failure.

SUMMARY

According to an embodiment of a delivery system for implanting a biostimulation device, a stylet extends along an axis from knob end to a threaded end configured to engage an internally threaded nut of the biostimulation device and a catheter tube configured to axially contain the stylet. The catheter tube comprises a feature that engages a corresponding feature on the biostimulation device whereby the stylet can be rotated relative to the catheter tube for disengagement of the stylet threaded end from the biostimulation device threaded end.

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

A delivery system can deploy leadless cardiac pacemakers equipped with either an active or passive fixation device. A first sheathed catheter system protects the fixation device and provides counter rotation to disengage the leadless cardiac pacemaker from the catheter. A second sheath-less catheter system includes a dissolvable, protective capsule covering the fixation device and a lumen providing counter-rotational force to disengage the leadless cardiac pacemaker from the catheter.

A delivery system is depicted which can be used with a biostimulation device, such as a leadless cardiac pacemaker.

A delivery system can be constructed that reduces the number of concentric elements forming a catheter.

For example, an embodiment of a delivery system can be used for implanting a leadless cardiac pacemaker inside the cardiac chamber in the human body. Embodiments include two delivery systems, for example a sheath and sheath-less approach, to safely deliver leadless cardiac pacemakers with active or passive fixation devices to the cardiovascular system.

In some embodiments, a delivery system can support rotational counter traction to enable disengagement of a stylet using a sheathed approach for protecting the implantable biostimulation device.

A delivery system that implements a sheathed technique for implantable device protection can be configured to enable retraction of the sheath for a pre-defined distance to expose pacemaker electrodes and permit threshold testing without completely disengaging a delivery catheter.

In other illustrative embodiments, a delivery system can employ rotational counter traction to enable disengagement of a stylet using a sheath-less approach for protecting the device. For example, a biocompatible, soluble, protective cover for the fixation devices can be used to prevent damage to the cardiovascular system.

Figure 1A:
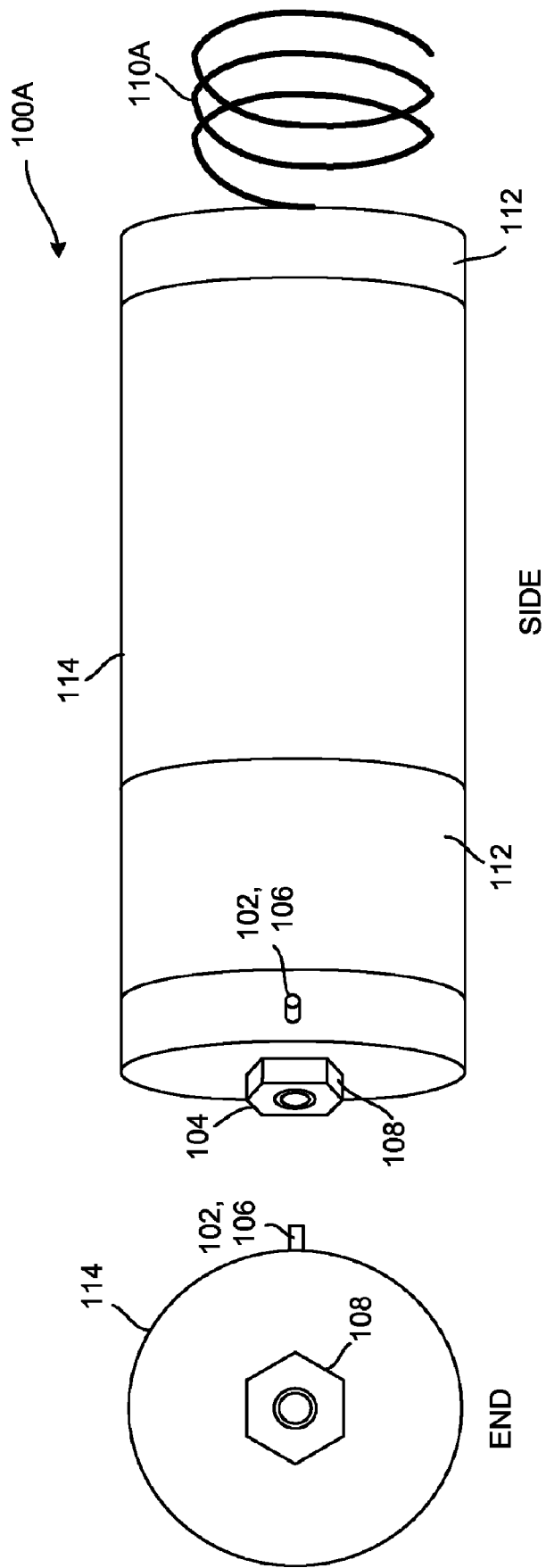
FIG. 1A is a pictorial diagram showing an embodiment of a leadless cardiac pacemaker with active fixation for use with a sheath catheter.
Figure 1B:
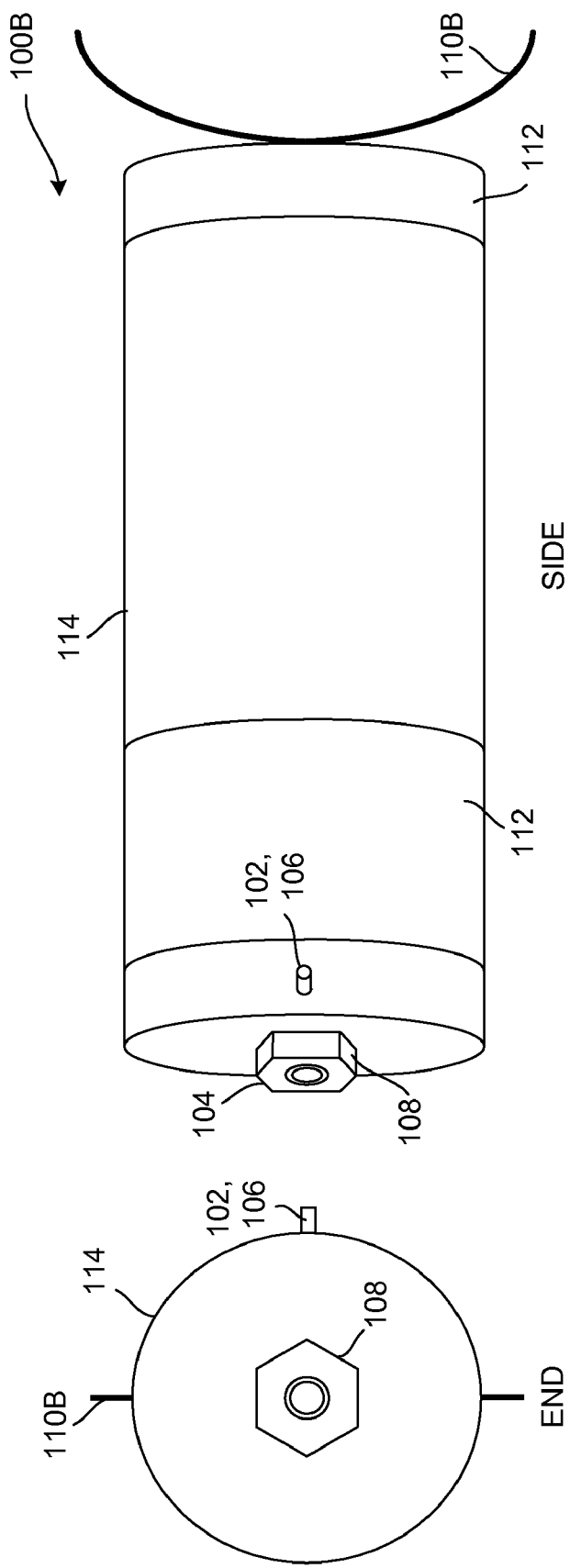
FIG. 1B is a schematic block diagram depicting an embodiment of a leadless cardiac pacemaker with passive fixation for use with a sheath catheter.
Figure 2:
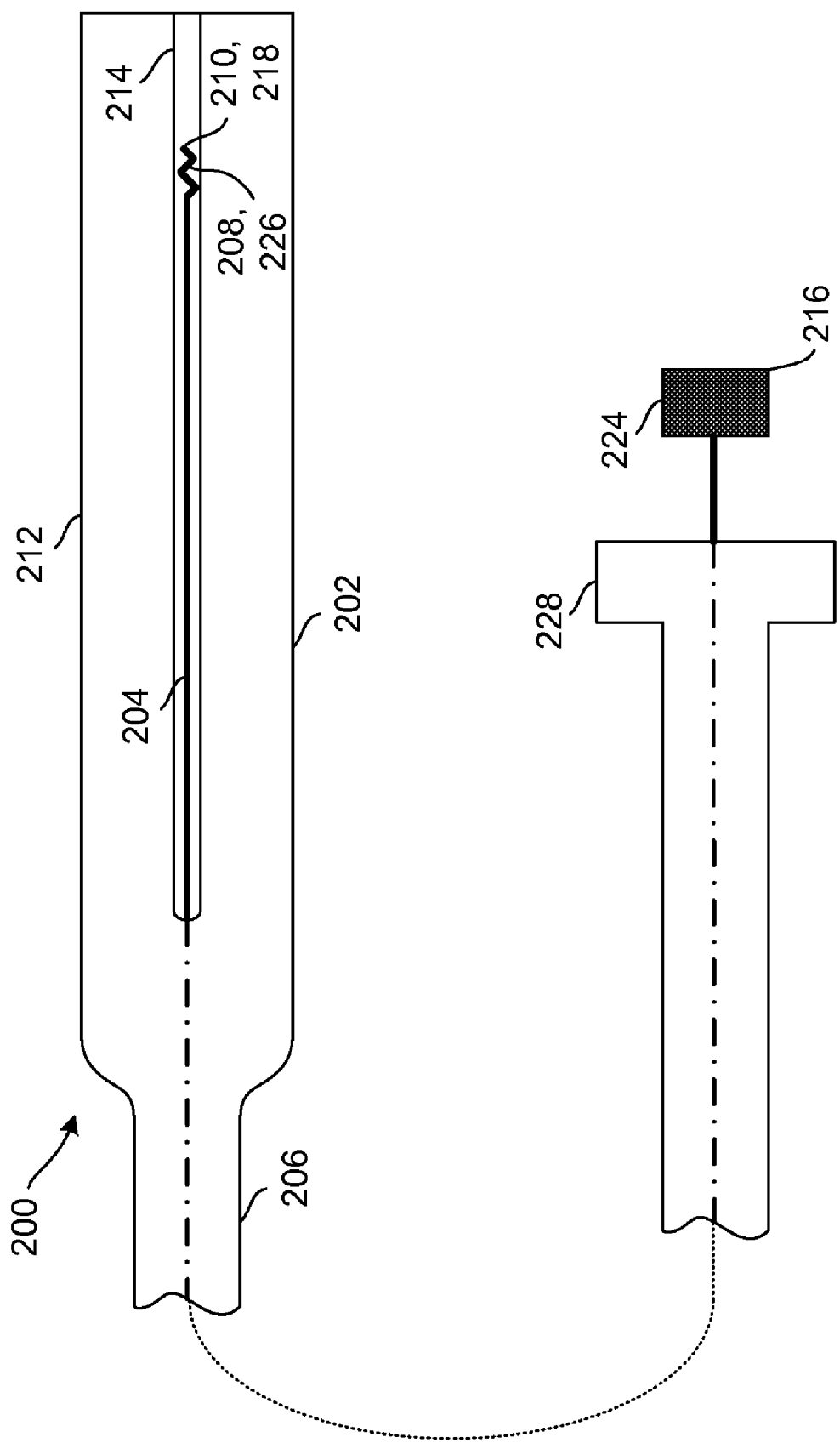
FIG. 2 is a pictorial diagram that illustrates an embodiment of a delivery catheter comprising a sheath and stylet.

Referring to FIGS. 1A and 1B, pictorial end and side views show embodiment of a leadless cardiac pacemaker 100A, 100B that can be delivered using a delivery apparatus. Referring to FIG. 2, a pictorial view illustrates an embodiment of a delivery apparatus 200 for delivering and implanting an implantable device, for example a leadless cardiac pacemaker 100A, 100B. The illustrative delivery apparatus 200 comprises a bi-concentric-axial element catheter 202 configured for engaging to and disengaging from the leadless cardiac pacemaker via relative motion of an internal stylet element 204 to an externally circumferential tube element 206.

As shown in FIG. 2 in combination with FIGS. 1A and 1B, the tube element 206 has a feature 208 that engages a corresponding feature 102 on the leadless cardiac pacemaker 100A, 100B whereby the stylet element 204 can be rotated relative to the tube element 206 for disengagement of a threaded end 210 of the stylet 204 from a threaded end 104 of the leadless cardiac pacemaker 100A, 100B.

FIG. 1A depicts a leadless cardiac pacemaker 100A with an active fixation device 110A. The leadless cardiac pacemaker 100A is contained within a cylindrical hermetic housing 114 and includes annular electrodes 112 at housing extremities. In one example of an active fixation device, a helix 110A provides active fixation when screwed into cardiac muscle. A stylet hex nut 108 enables the delivery catheter 202 to attach to the leadless cardiac pacemaker 100A during deployment. One or more alignment pins 106 are attached to the hermetic housing 114.

FIG. 1B illustrates a leadless cardiac pacemaker 100B with a passive fixation device 110B, depicted with tines 110B shown expanded and facilitate lodging of the leadless cardiac pacemaker 100B inside a cardiac vessel during the first few weeks after implantation. The tines 110B are commonly made from a biocompatible polymer such as polyurethane or medical grade silicone and may have many various shapes and forms.

FIG. 2 illustrates a sheathed embodiment of a delivery apparatus 200. The tube element 206 can comprise a sliding sheath 212 configured to axially slide over the stylet 204 and engaged leadless cardiac pacemaker 100A, 100B and configured to protect patient tissue from damage during insertion of the leadless cardiac pacemaker. The sliding sheath 212 has a feature 214 that engages a corresponding feature 106 on the leadless cardiac pacemaker 100A, 100B whereby the stylet 204 can be rotated relative to the sliding sheath 212 for disengagement of the threaded end 210 of the stylet 204 from the threaded end 104 of the leadless cardiac pacemaker 100A, 100B.

The sheath/stylet delivery catheter 202 shown in FIG. 2 is an assembly comprising a sheath 212 and a stylet 204. At the distal end 218 of stylet 204 is screw 226. At the proximal end 216 of the stylet wire 204 is a knob 224 which enables the screw 226 to be inserted into a stylet hex nut 108 shown in FIGS. 1A, 1B and 2. The stylet 204 can be formed from a biocompatible metal such as stainless steel. The stylet knob 224 can be formed from a rigid plastic. The sheath 212 can be formed from extruded Teflon, polytetrafluoroethylene, polyolefin, polyvinyl chloride, or polyurethane and contains one or more slots 214. A sheath knob 228 can be formed from rigid plastic. Elements and components of the sheath/stylet catheter 202 can be constricted from any suitable material in addition to the materials specifically described herein.

Accordingly, FIGS. 1A, 1B, and 2 describe a leadless cardiac pacemaker (LCP) delivery system used to deploy a LCP with active 100A or passive 100B fixation using a sheath catheter 206. The LCP 100A, 100B connects to a catheter 206 containing a stylet 204 and sheath assembly 212. The stylet 204 screws into a hex nut 108 attached to the end of the LCP 100A, 100B. The sheath 212 includes a feature 214 that, when aligned with a guide pin 106 on the LCP 100A, 100B, enables application of a counter-rotational force for disengaging the locking stylet 204. The sheath 212 protects the cardiovascular system from damage during insertion from the fixation devices 110A, 110B and includes a feature 214 enabling the catheter 206 to rotate the LCP 100A, 100B. Once positioned the catheter assembly 206 can be rotated to affix the active fixation screw 110A in the case of active fixation. The sheath 212 is then partially withdrawn to allow pacing and sensing threshold measurements. After confirming the LCP position, the stylet 204 can be unscrewed and withdrawn, followed by the sheath 212, leaving the LCP 100A, 100B in the selected position.

Figure 3A:
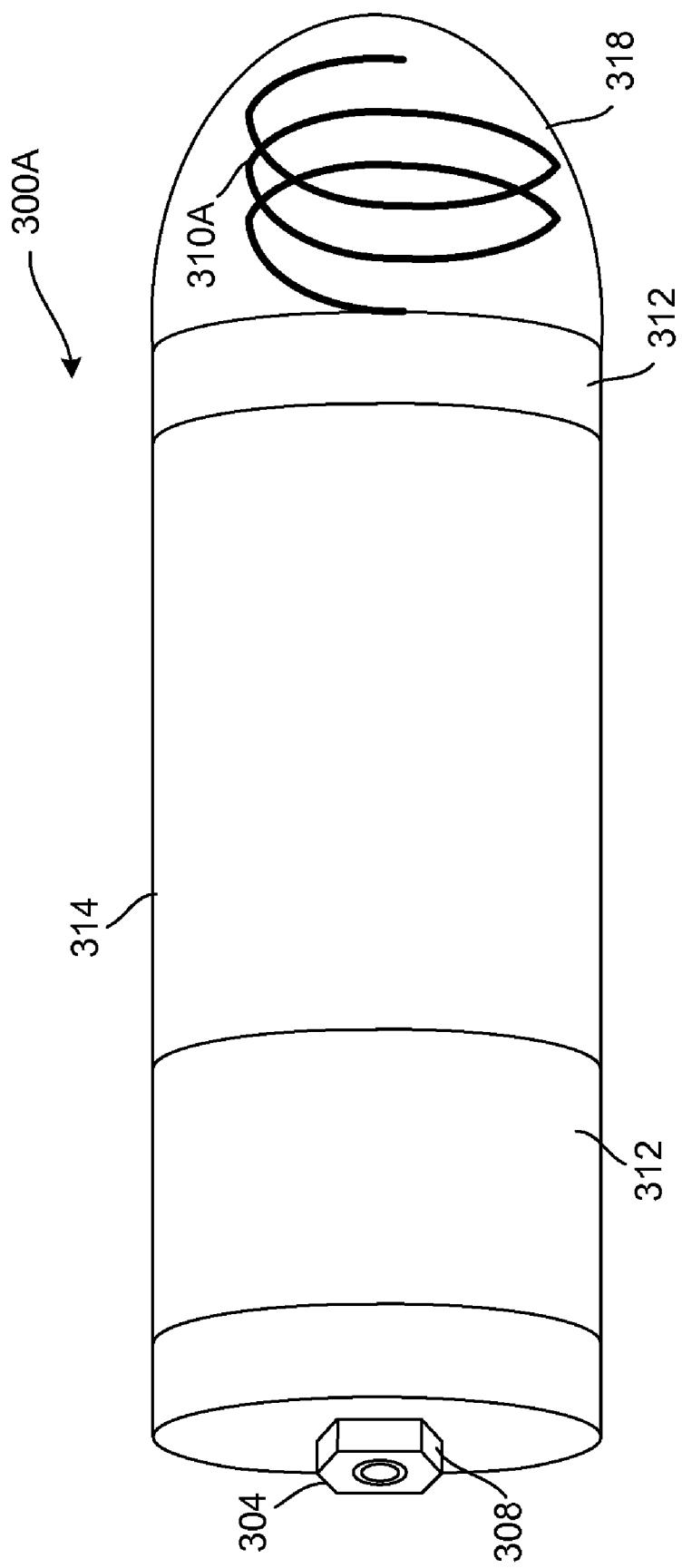
FIG. 3A is a pictorial diagram showing an embodiment of a leadless cardiac pacemaker with active fixation for use with a sheath catheter.
Figure 3B:
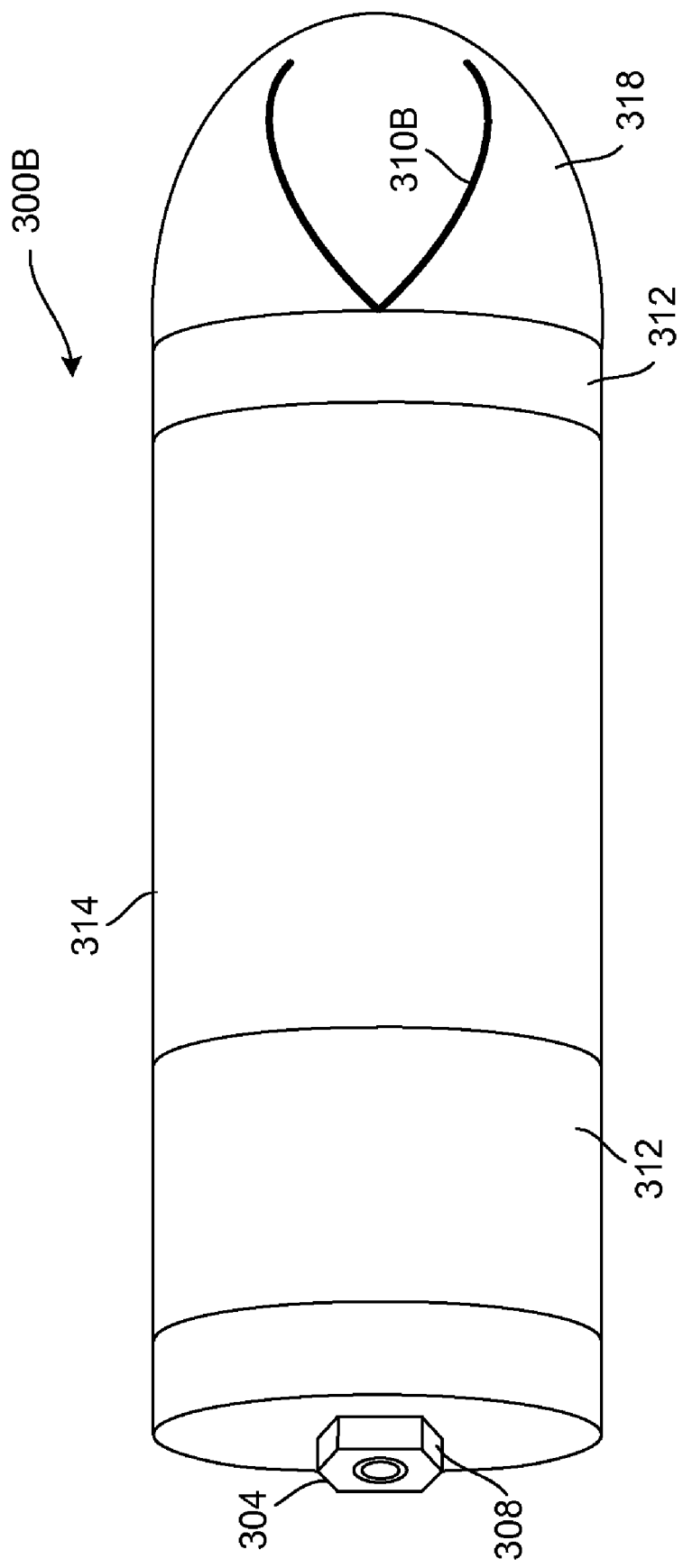
FIG. 3B is a pictorial diagram showing an embodiment of a leadless cardiac pacemaker with a soluble cap over the passive fixation for use with a sheath-less catheter.
Figure 4:
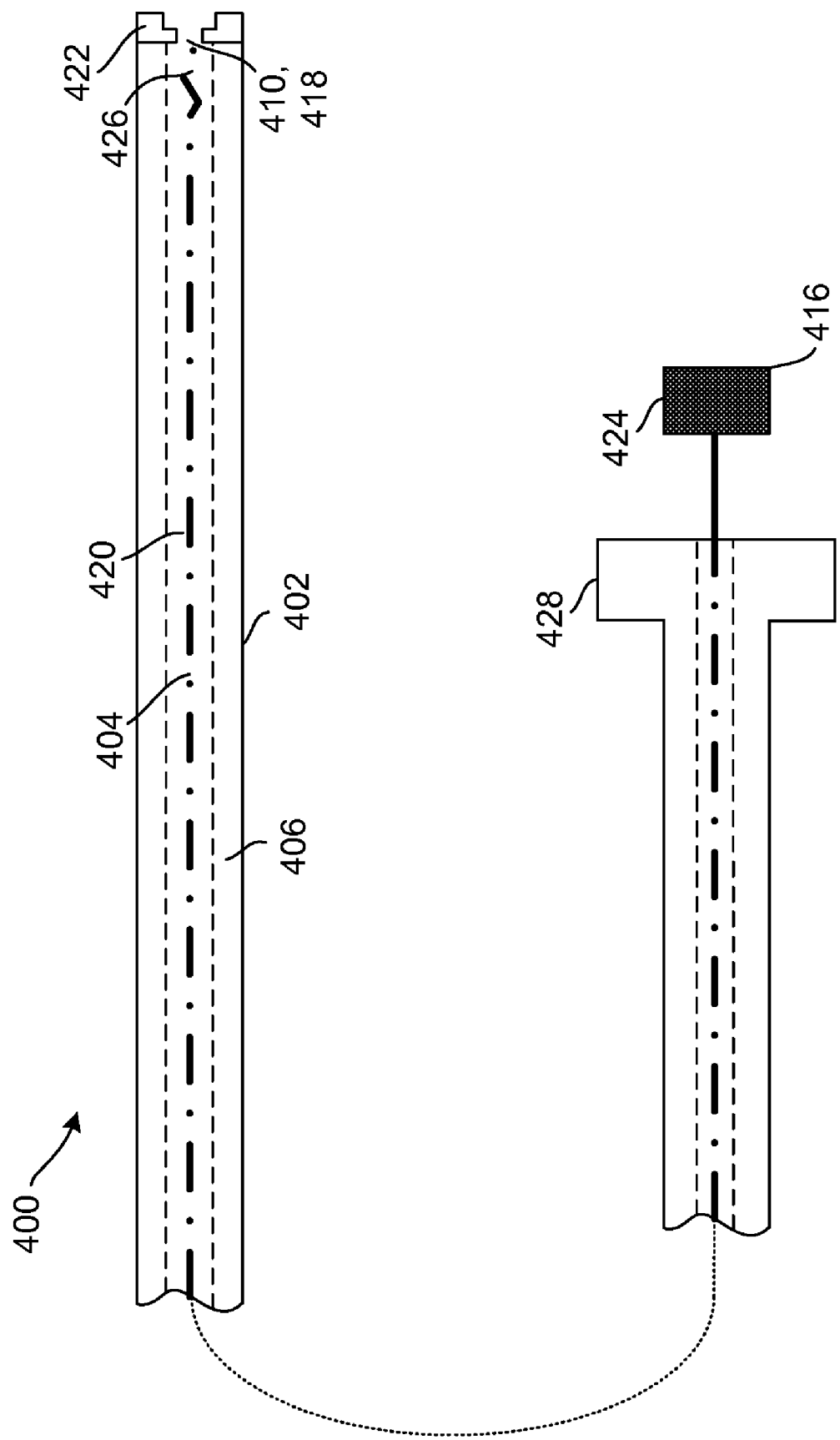
FIG. 4 is a pictorial diagram that illustrates an embodiment of a delivery catheter for usage in delivery in implantable device using a sheath-less approach.

Referring to FIGS. 3A and 3B, pictorial side views show embodiment of a leadless cardiac pacemaker 300A, 300B that can be delivered using a sheath-less delivery apparatus. Referring to FIG. 4, a pictorial view illustrates an embodiment of a sheath-less delivery apparatus 400 adapted to deliver and implant an implantable device such as a leadless cardiac pacemaker 300A, 300B. The illustrative sheath-less delivery apparatus 400 has a bi-concentric-axial element catheter 402 that engages and disengages from the leadless cardiac pacemaker by motion of an internal stylet element 404 relative to an externally circumferential tube element 406. The tube element 406 comprises a sheath-less catheter 402 that extends axially from a knob end 416 to a socket end 418 and encloses an internal lumen 420. The sheath-less catheter 402 is configured to axially slide over the stylet 404 and engage the leadless cardiac pacemaker 300A, 300B. The sheath-less catheter 402 comprises a socket 422 at the socket end 418 that engages a corresponding nut 308 on the leadless cardiac pacemaker 300A, 300B so that the stylet 404 can be rotated relative to the sheath-less catheter 402 for disengagement of the threaded end 410 of the stylet 404 from the threaded end 304 of the leadless cardiac pacemaker 300A, 300B. A biocompatible soluble protective covering 318 can be adapted to cover a fixation member 310A, 310B coupled to the leadless cardiac pacemaker 300A, 300B during insertion of the leadless cardiac pacemaker 300A, 300B into a patient's body whereby the patient's body tissue is protected.

Another embodiment of a delivery system 400 is sheath-less and includes a tube element 406 with internal lumen 420 and stylet catheter 402 to deliver the LCP 300A, 300B to a selected site. The fixation mechanism 310A, 310B on the LCP 300A, 300B is protected using a biocompatible, soluble coating 318 during deployment. FIGS. 3A and 3B depict the leadless cardiac pacemaker with an active fixation 300A and passive fixation 300B device respectively protected using mannitol or other sugar derivates. Other materials may also or otherwise used that can form a protective capsule at room temperature, dissolve when implanted yet have no toxic side-effects.

The lumen/stylet delivery catheter 400 is shown in FIG. 4. The assembly 400 comprises of a tube element 406 enclosing a lumen 420, a stylet 404, a stylet knob 428, and lumen assembly knob 424. The distal end 418 of the stylet 404 contains a threaded screw 426 for insertion into the stylet hex nut 308. Also shown is hex nut socket 422 which is bonded to the distal end 418 of the lumen assembly 406 and adapted to receive the external features of the stylet hex nut 308 attached to the LCP 300A, 300B. The hex nut socket 422 prevents counter rotation of the LCP 300A, 300B and lumen assembly 406 when engaged. The tube element 406 enclosing the lumen 420 can be extruded from polyurethane or silicone. The lumen assembly knob 428 is typically made from polyurethane or rigid plastic. The stylet 404 can be made from stainless steel. The stylet knob 224 is typically made from rigid plastic. The diameter of the lumen 420 is typically the same or inferior to the diameter of the LCP 300A, 300B. Other suitable materials may be substituted for the material specifically disclosed herein.

FIG. 4 depicts an LCP delivery system 400 that can be used to deploy a LCP with active 300A or passive 300B fixation using a sheath-less catheter 402 wherein the LCP 300A, 300B connects to a catheter 402 containing a stylet 404 and lumen assembly 420. The stylet 404 screws into a hardware element such as a hexagonal or other polygonal sided nut 308 attached to the end of the LCP 300A, 300B. Counter-rotation can be enabled via a plastic locking polygonal-sided socket, for example a hex socket 422, attaches to the lumen assembly 420 and engages the LCP polygonal-sided nut, for example hex nut 308. To protect the cardiovascular system from damage during insertion the fixation devices 310A, 310B are coated with a biocompatible soluble protective covering 318 such as mannitol. Once positioned, the protective covering 318 dissolves and the catheter assembly 402 can be rotated to affix the active fixation screen 310A in the case of active fixation. Pacing and sensing threshold measurement can then be performed. After the LCP 300A, 300B position is confirmed, the stylet 404 can be unscrewed and withdrawn, followed by the lumen assembly 420, leaving the LCP 300A, 300B in a selected position.

FIGS. 2 and 4 depict two leadless cardiac pacemaker delivery systems 200, 400. The first system 200 uses a sheath 212 and stylet catheter 202. The second system 400 uses a lumen assembly 420 and stylet catheter 402 in combination with a biocompatible, soluble, protective coating 318 applied to the leadless cardiac pacemaker 300A, 300B. Either approach can be used with an active fixation or passive fixation element to anchor the leadless cardiac pacemaker to the desired site.

In addition, both delivery systems 200, 400 can be combined with other tools and techniques commonly used to obtain access to the cardiovascular venous system, such as introducers, guide-wires, dilators and other tools to gain access to locations commonly used to provide cardiac pacing therapy.

Referring again to FIG. 2 in combination with FIGS. 1A and/or 1B, an embodiment of a delivery system 200 is depicted which is configured for implanting a biostimulation device 100A, 100B. The delivery system 200 comprises a stylet 204 and a catheter tube 206. The stylet 204 extends along an axis from knob end 214 to a threaded end 216 and is configured to engage an internally threaded nut 108 of the biostimulation device 100A, 100B.

The catheter tube 206 is configured to axially contain the stylet 204 and comprises a feature 208 that engages a corresponding feature 102 on the biostimulation device 100A, 100B whereby the stylet 204 can be rotated relative to the catheter tube 206 for disengagement of the threaded end 208 of the stylet 204 from the threaded end 104 of the biostimulation device 100A, 100B.

As shown in the embodiment depicted in FIG. 2, a sliding sheath assembly 212 is configured to axially slide over the stylet 204 and the engaged biostimulation device 100A, 100B. The sliding sheath assembly 212 comprising a feature 212 that engages a corresponding feature 106 on the biostimulation device 100A, 100B whereby the stylet 204 can be rotated relative to the sliding sheath 212 for disengagement of the threaded end 208 of the stylet 204 from the threaded end 104 of the biostimulation device 100A, 100B. The sliding sheath 212 is configured to protect patient tissue from damage during insertion of the biostimulation device 100A, 100B. The sliding sheath 212 further comprises a feature 212 configured to engage and rotate the biostimulation device 106 and to affix a fixation member 110A, 110B coupled to the biostimulation device 100A, 100B into patient tissue. The engaging feature 212 of the sliding sheath assembly 212 is configured to enable rotational counter traction for disengagement of the stylet 204.

In some embodiments, the sliding sheath assembly 212 can be configured to axially retract from the stylet 204 a predetermined distance so that electrodes 112 of the biostimulation device 100A, 100B are exposed, enabling threshold testing while the biostimulation device 100A, 100B remains engaged to the stylet 204.

In the illustrative embodiment, the catheter 202 comprises a tube element 206 and a sheath 212. The sheath 212 is configured with a sheath slot 214 configured to align with an alignment pin 106 of the biostimulation device 100A, 100B that prevents rotation of the biostimulation device 100A, 100B with respect to the sheath 212. The stylet 204 extends along the axis from a knob 224 coupled to a proximal end 216 to a screw 226 coupled to the distal end 218. The stylet 204 is configured so that for the knob 224 to be fully retracted, the biostimulation device 100A, 100B is fully contained within the sheath 212 and a fixation member 110A, 110B coupled to the biostimulation device 100A, 100B is protected. The stylet 204 is further configured so that for a condition that the knob 224 is fully depressed, the alignment pin 106 is contained within the sheath 212 and electrodes 112 of the biostimulation device 100A, 100B are fully exposed, enabling threshold testing before disengagement.

Referring to FIG. 4 in combination with FIGS. 3A and/or 3B, a catheter tube assembly 402 extends from a knob end 416 to a socket end 418 and encloses an internal lumen 420 configured to axially slide over the stylet 404 and engage the biostimulation device 300A, 300B. The catheter tube assembly 402 comprises a socket 422 at the socket end 418 that engages a corresponding nut 308 on the biostimulation device 300A, 300B whereby the stylet 404 can be rotated relative to the catheter tube assembly 402 for disengagement of the stylet threaded end 410 from the biostimulation device threaded end 304. The stylet 404 can be configured to screw into a multiple-sided nut 308 attached to the biostimulation device 100A, 100B and the socket 422 can be configured as a locking hex socket that engages the multiple-sided nut 308 on the biostimulation device 300A, 300B whereby the stylet 404 and socket 422 are configured to enable counter-rotation of the stylet 404 relative to the biostimulation device 300A, 300B.

In the embodiment depicted in FIG. 4 in combination with FIGS. 3A and 3B, the catheter tube assembly 402 is a sheath-less catheter and the biostimulation device 300A, 300B can be a leadless cardiac pacemaker with the delivery system 400 configured to deploy the leadless cardiac pacemaker with active 310A or passive 310B fixation using the sheath-less catheter 402.

A sheath-less catheter socket 422 can comprise a socket adapted to enable rotational counter traction for stylet disengagement. A biocompatible soluble protective covering 318 configured to cover a fixation member 310A, 310B can be coupled to the biostimulation device 300A, 300B during insertion of the biostimulation device into a patient's body whereby the patient's body tissue is protected. In various embodiments, the biocompatible soluble protective covering 318 can comprise mannitol, polyvinylpyrrolidone, a protective salt, or other suitable material.

The biocompatible soluble protective covering 318 is most suitably selected to comprise a material that forms a protective capsule at room temperature, dissolves when implanted, and has no toxic side effects. For example, the biocompatible soluble protective covering 318 can be selected to dissolve in a selected time after which a fixation device 310A, 310B coupled to the biostimulation device 300A, 300B is exposed. The fixation device 310A, 310B is typically advanced by rotating the catheter tube assembly 402 and the stylet 404 until the biostimulation device 300A, 300B is anchored.

In the illustrative embodiment, the catheter tube assembly 402 circumferentially encloses an inner lumen 420 and the stylet 404 extending through the lumen 420. The catheter tube assembly 402 comprises a catheter knob 424 at a proximal end 416 and a multiple-sided nut socket 422 at a distal end 418 of the catheter tube assembly 402. The multiple-sided nut socket 422 is configured to receive external features of a multiple-sided nut 308 coupled to the biostimulation device 300A, 300B. The multiple-sided nut socket 422 and biostimulation device's multiple-sided nut 308 are formed to prevent counter-rotation of the biostimulation device 300A, 300B and the catheter tube assembly 402 when engaged. The stylet 404 comprising a stylet knob 424 at a proximal end 416 and a threaded screw 426 at a distal end 418 of the stylet 404. The threaded screw 426 is configured for engaging the internally threaded nut 308 of the biostimulation device 300A, 300B.

In a particular sample embodiment, the catheter tube assembly 402 can be extruded from polyurethane, polytetrafluoroethylene, polyolefin, polyvinyl chloride or silicone. The diameter of the catheter tube assembly 402 can be smaller than or equal to the biostimulation device diameter. For example, the catheter knob 424 can be constructed from rigid plastic or metal and the stylet 404 constructed from stainless steel. Typically, the stylet knob 424 can be constructed from rigid plastic or metal. Elements and components of the catheter tube assembly 402 can be constructed from any suitable material in addition to the materials specifically identified herein.

The biostimulation device 300A, 300B can be configured as a leadless cardiac pacemaker.

In various embodiments, for example the structures depicted in FIGS. 2 and 4, the stylet 204, 404 and the catheter tube 206, 406 comprise the delivery system 200, 400 whereon two concentric members alone form a catheter 202, 402. The stylet 204, 404 and the catheter tube 206, 406 are configured for implanting the biostimulation device which is adapted for either active or passive fixation to patient tissue. In some embodiments, a radio-opaque marker can be adapted for coupling to the stylet 204, 404, the catheter tube 206, 406, and/or the biostimulation device for identification under fluoroscopy and facilitation of positioning.

Figure 5:
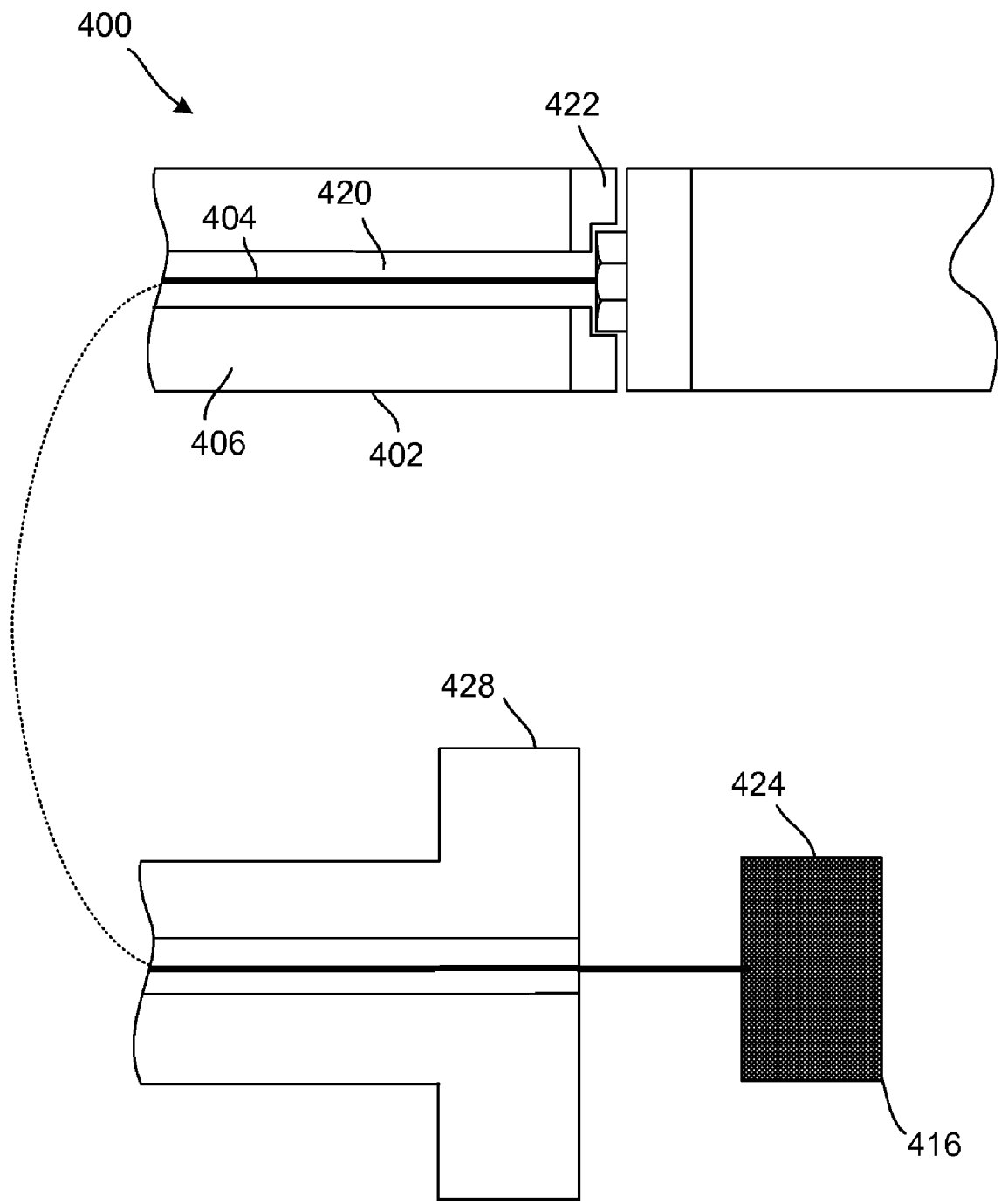
FIG. 5 is a pictorial diagram illustrating a cross-sectional view of an embodiment of a lumen assembly and stylet delivery catheter.
Figure 6A:
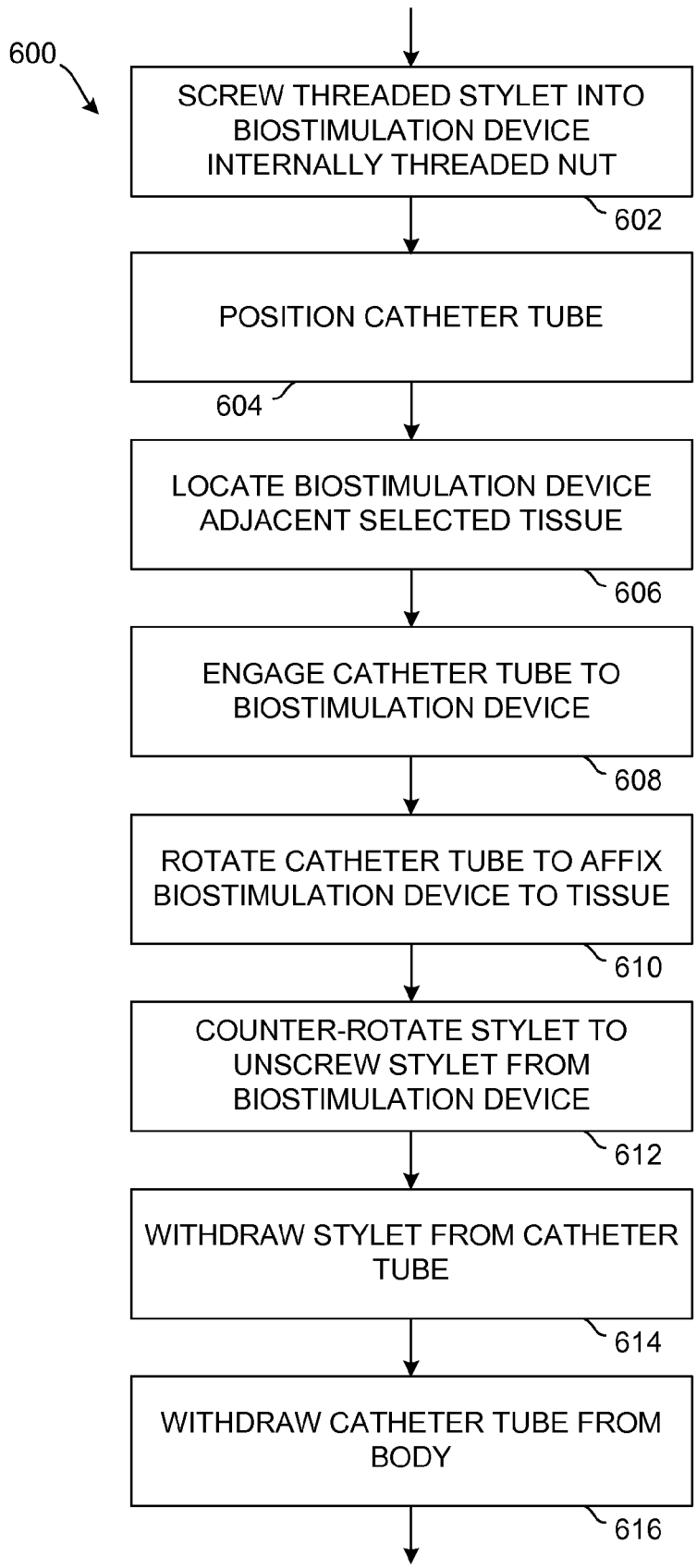
FIGS. 6A through 6E are flow charts depicting embodiments of methods for implanting a biostimulation device in patient body tissue.

Referring to FIG. 6A in combination in the context of FIGS. 1 through 5, a flow chart depicts an embodiment of a method 600 for implanting a biostimulation device 100A, 100B, 300A, 300B in patient body tissue. The method 600 comprises screwing 602 a threaded end of a stylet into an internally threaded nut of the biostimulation device and positioning 604 the catheter tube to locate 606 the biostimulation device adjacent a selected patient body tissue. A feature of the catheter tube is engaged 608 against a corresponding feature on the biostimulation device so that rotation of the catheter tube rotates the biostimulation device relative to the patient body tissue. The catheter tube is rotated 610 to affix the fixation device on the biostimulation device to the patient body tissue. The stylet is counter-rotated 612 relative to the catheter tube to unscrew the threaded end of a stylet from the internally threaded nut of the biostimulation device.

The stylet can be withdrawn 614 from the catheter tube and the catheter tube withdrawn 616 from the patient's body. In a typical embodiment, the biostimulation device can be a leadless cardiac pacemaker and the patient body tissue for implanting the pacemaker is cardiac tissue.

Figure 6B:
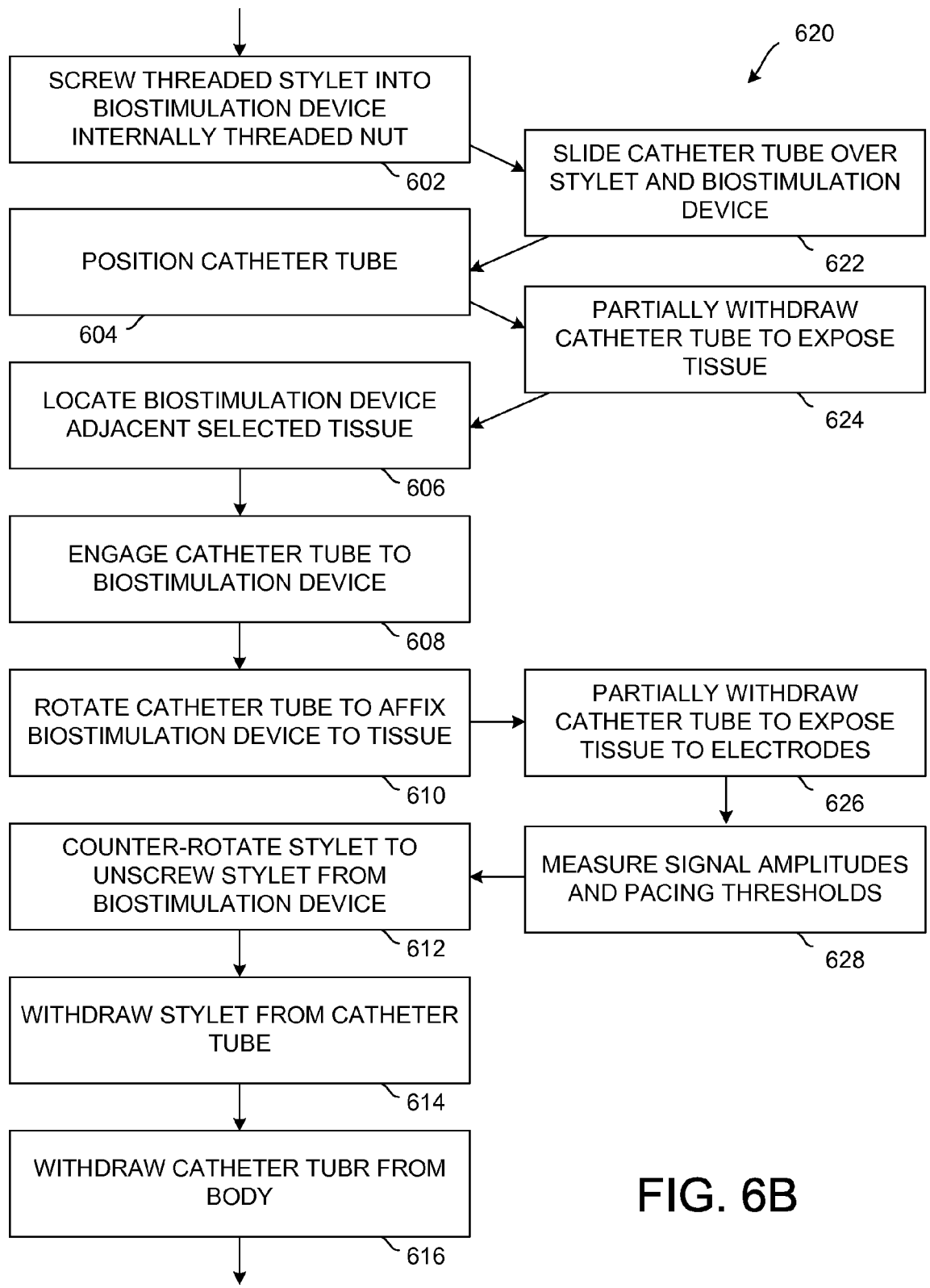

Referring to FIG. 6B, in some embodiments a method 620 can further comprise, prior to positioning 604 the catheter tube, axially sliding 622 a catheter tube over the stylet and the biostimulation device so that the stylet and biostimulation device are internally contained within the catheter tube. Also in various embodiments, prior to locating 606 the biostimulation device adjacent the selected patient body tissue, the catheter tube can be partially withdrawn 624 the catheter tube to expose patient body tissue to the fixation device on the biostimulation device for affixation. Prior to unscrewing 612 the stylet from the biostimulation device, the catheter tube can be partially withdrawn 626 to expose patient body tissue to biostimulation device electrodes so that signal amplitudes and pacing thresholds of the biostimulation device can be measured 628. According to the measurements, the biostimulation device can be repositioned and parameters retested until measurements attain predetermined levels.

The lumen/stylet catheter 402 depicted in FIG. 4 or 5 can be used to place a LCP 300A, 300B in the cardiovascular system. Once located, in the case of an LCP 300A with active fixation, the LCP is advanced to the desired location and time is allowed for the protective coating to dissolve thus exposing the helix 310A. Once exposed, the helix 310A is advanced by rotating both the lumen assembly knob 428 and stylet knob 424 until the LCP 300A is anchored. Unlike the sheath/stylet catheter 200, catheter pacing and sensing tests can be performed immediately.

As with both active and passive fixation LCPs 300A, 300B, the lumen/stylet catheter 400 can be disengaged by holding the lumen assembly knob 428 and rotating the stylet knob 424 to unscrew the stylet 404 from the stylet hex nut 308. After the screw 426 and nut 308 are apart, the lumen/stylet catheter 402 can be retracted.

Figure 6C:
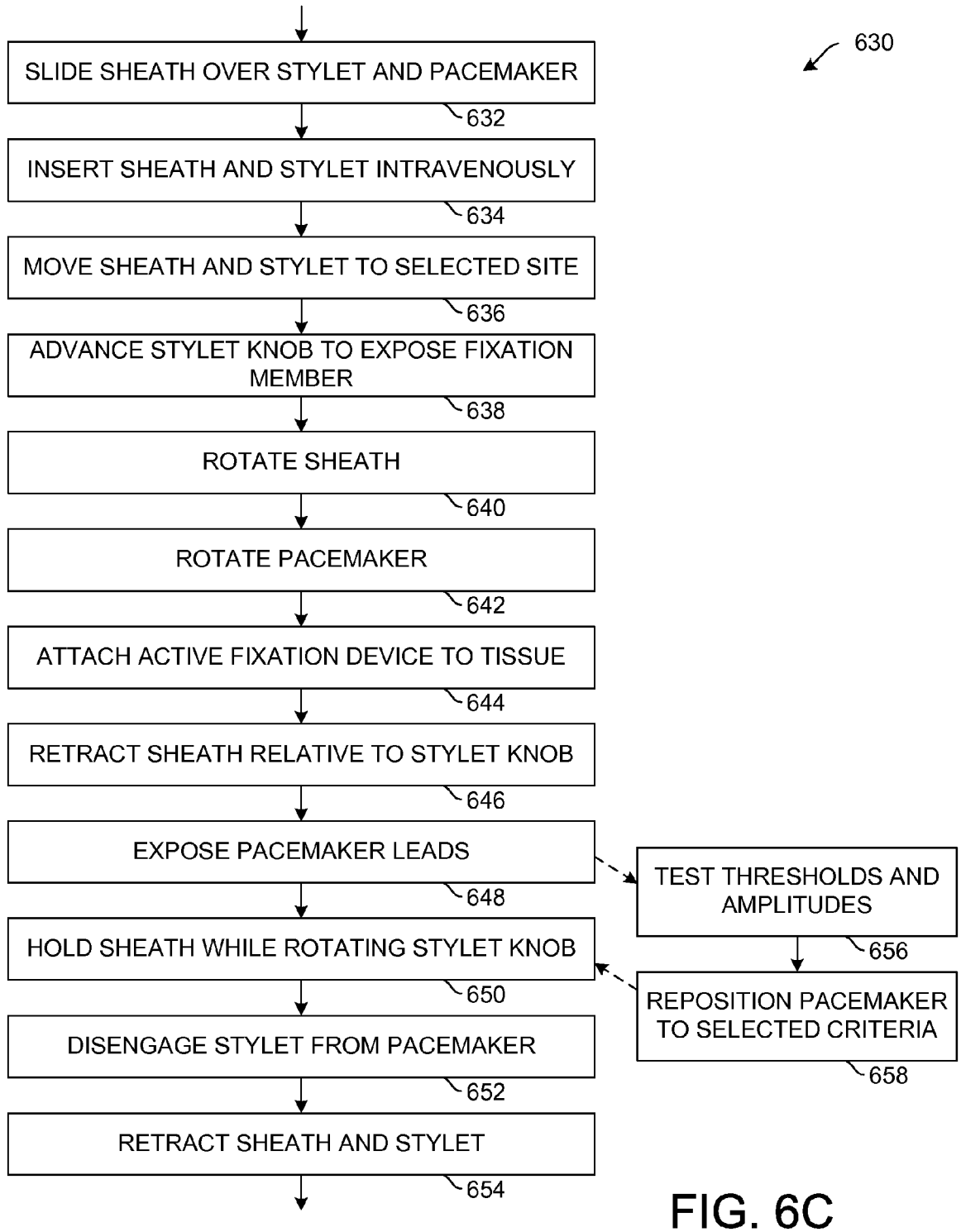

Referring to FIG. 6C in combination in the context of FIGS. 1A and 2, a flow chart depicts an embodiment of a method 630 for implanting a biostimulation device 100A in patient body tissue using a sheathed delivery system and active fixation.

In typical usage of the sheath/stylet catheter system 200 for use with a LCP 100A configured with active fixation 110A, initially the stylet hex nut 108 connects to the stylet screw 226 shown in FIGS. 1A and 2, respectively. When the stylet knob 216 is fully retracted, the LCP 100A is fully contained within the sheath 212 protecting the helix 110A. The LCP 100A alignment pin 106 aligns with the sheath slot 214 to prevent rotation of the LCP 100A with respect to the sheath 212. When the stylet knob 216 is fully depressed the alignment pins 106 on the LCP 100A remain within the sheath 212, however both electrodes 112 are fully exposed, enabling testing of the LCP 100A before disengagement.

The sheath/stylet catheter system 200 and LCP 100A can be inserted intravenously either in the cephalic, subclavian, or femoral vein and moved progressively towards the heart until the distal end of the sheath 212 reaches the selected site. An LCP 100A with active fixation is typically implanted in either the right atrium or ventricle. When the selected position is obtained, the stylet knob 224 is advanced gently to expose the helix screw 226. The sheath knob 228 is then used to rotate the entire assembly 200 enabling the helix 110A to attach to the cardiac muscle.

When the LCP 100A is sufficiently anchored, the sheath knob 228 is pulled back relative to the stylet knob position to expose both electrodes 112. Pacemaker testing can be performed with the implanted LCP 100A while still connected to the delivery system 200. When adequate pacing thresholds and signal amplitudes have been verified, the catheter system 202 can be disengaged from the LCP 100A by holding the sheath knob 228 and rotating the stylet knob 224 to unscrew the stylet 204 from the stylet hex nut 108. Once the screw 226 and nut 108 are apart, the sheath/stylet catheter 202 can be retracted.

The method 630 comprises axially sliding 632 a sheath over the stylet and a leadless cardiac pacemaker so that the stylet and leadless cardiac pacemaker with active fixation member are internally contained within the sheath. The sheath and stylet combination are inserted 634 intravenously either in a cephalic, subclavian, or femoral vein of a patient. The sheath and stylet combination are progressively moved 636 towards patient cardiac tissue until a distal end of the sheath reaches a selected site of the cardiac tissue. At the selected site, a stylet knob is gently advanced 638 into the sheath to expose the active fixation member coupled to the leadless cardiac pacemaker. The sheath is rotated 640, thereby rotating 642 the leadless cardiac pacemaker and attaching 644 the active fixation member to the cardiac tissue. Upon sufficient attachment of the active fixation member, the sheath is retracted 646 relative to the stylet knob, exposing 648 electrodes of the leadless cardiac pacemaker. The sheath is held 650 while rotating the stylet knob, unscrewing and disengaging 652 the stylet from the leadless cardiac pacemaker. The sheath and stylet combination is retracted 654 from the patient's cephalic, subclavian, or femoral vein.

After exposure 648 of leadless cardiac pacemaker leads, implanted leadless cardiac pacemaker pacing thresholds and signal amplitudes can be tested 656 and the leadless cardiac pacemaker repositioned 658 until the pacing thresholds and signal amplitudes meet selected criteria.

Figure 6D:
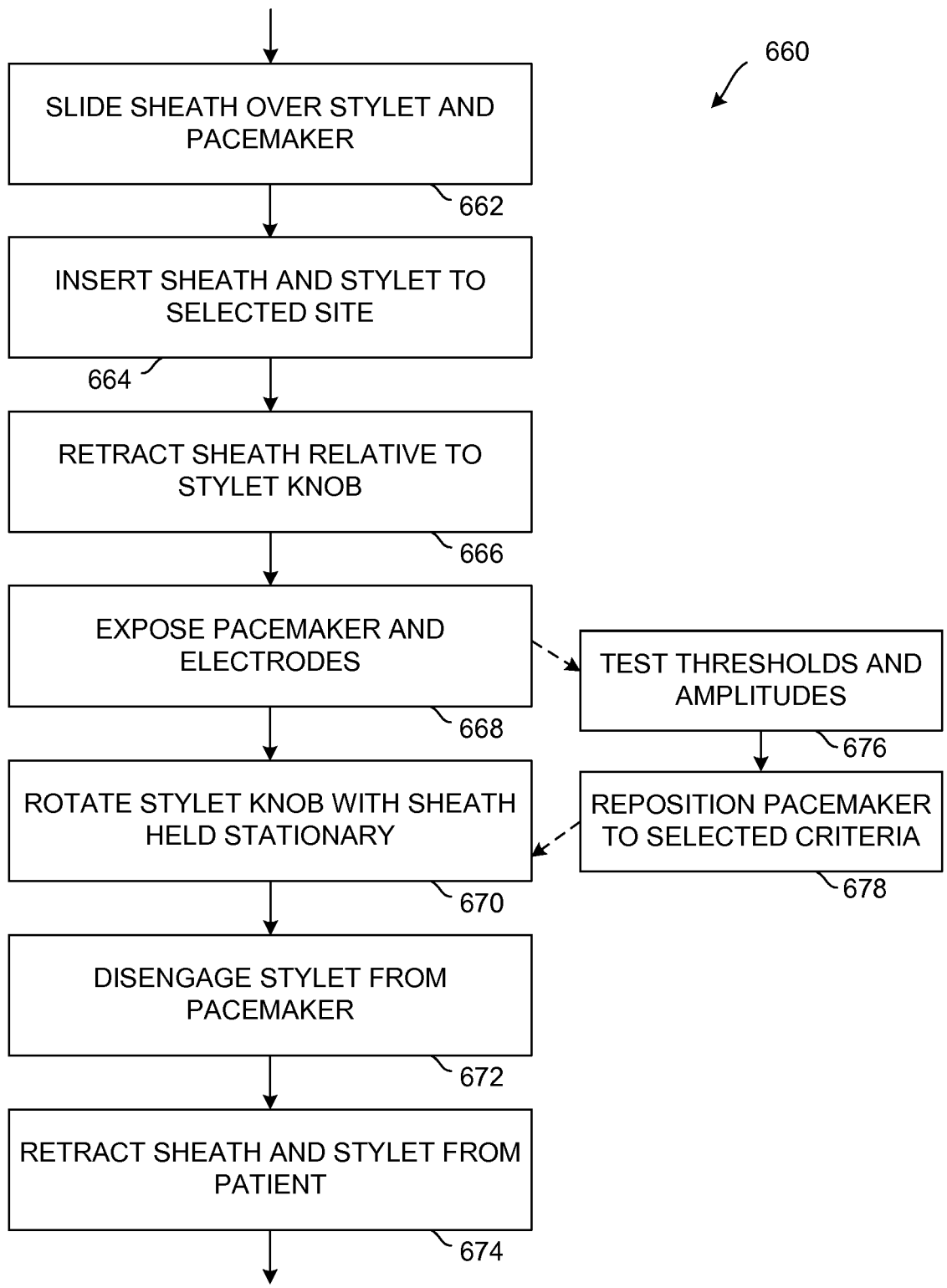

Referring to FIG. 6D in combination in the context of FIGS. 1B and 2, a flow chart depicts an embodiment of a method 660 for implanting a biostimulation device 100B in patient body tissue using a sheathed delivery system and passive fixation.

In typical usage of the sheath/stylet catheter system 200 for use with a LCP 100B configured with active fixation 110B, the LCP 100B and tines 110B are fully contained within the sheath 212 when the stylet knob 224 is fully retracted. Because LCP 100B with passive fixation devices 110B are typically located in the coronary sinus, the sheath/stylet catheter system 200 is typically used with a coronary sinus introducer system in which a guide wire is first inserted and positioned under fluoroscopy to the desired location. A dilator and introducer can be advanced over the guide wire. Once fully inserted, the dilator and guide wire are removed, leaving the introducer. The sheath/stylet catheter assembly 200 including the LCP 100B can then be advanced to the selected position. The LCP 100B advances ahead of the introducer to enable exposure of the LCP electrodes 112 to tissue once the sheath 212 is retracted. To expose the LCP 100B and expose both electrodes 112 the sheath knob 228 are pulled back relative to the stylet knob position. After pacemaker testing confirms the correct placement of the LCP 100B, the stylet 204 can be disengaged from the LCP 100B by holding the sheath knob 228 and rotating the stylet knob 224. After the screw 226 and nut 108 are apart, both the introducer and sheath/stylet catheter 202 can be retracted.

The method 660 comprises axially sliding 662 a sheath over the stylet and a leadless cardiac pacemaker so that the stylet and leadless cardiac pacemaker with passive fixation member are internally contained within the sheath. The sheath and stylet are inserted 664 in combination to a selected location of a patient's body tissue and, at the selected site, the sheath is gently retracted 666 relative to the stylet knob position, exposing 668 the leadless cardiac pacemaker and the electrodes. The stylet knob is rotated 670 while holding the sheath stationary, disengaging 672 the stylet from the leadless cardiac pacemaker and retracting 674 the sheath and stylet combination from the patient.

After exposure 668 of leadless cardiac pacemaker leads, implanted leadless cardiac pacemaker pacing thresholds and signal amplitudes can be tested 676 and the leadless cardiac pacemaker repositioned 678 until the pacing thresholds and signal amplitudes meet selected criteria.

Figure 6E:
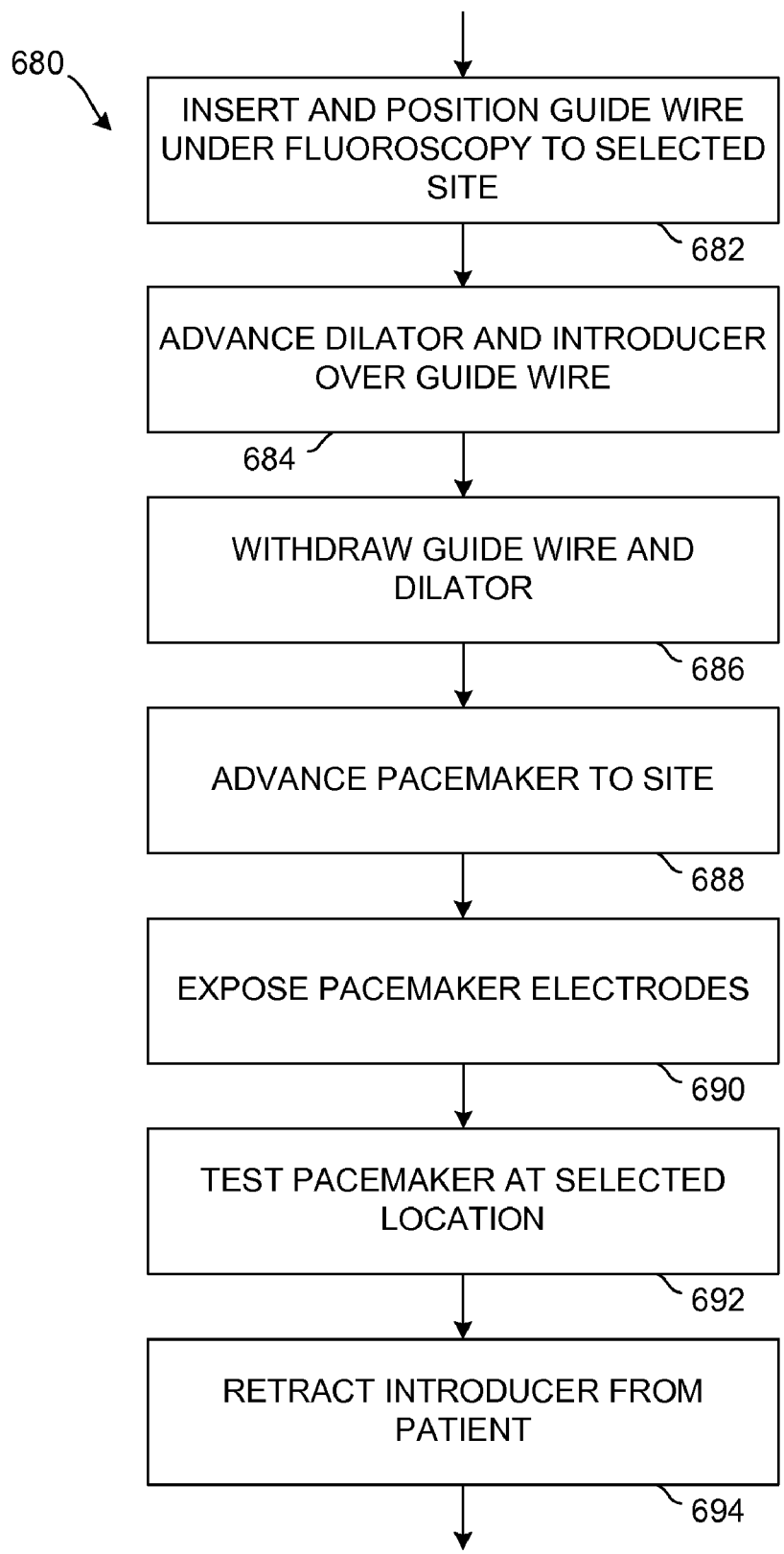

Referring to FIG. 6E in combination in the context of FIGS. 1B and 2, a flow chart depicts another embodiment of a method 680 for implanting a biostimulation device 100B in patient body tissue using a sheathed delivery system and passive fixation. The method 680 comprises inserting and positioning 682 a guide wire under fluoroscopy imaging to a selected location in a patient's coronary sinus using a coronary sinus introducer system and advancing 684 a dilator and introducer over the guide wire to the selected location. The guide wire can be withdrawn 686 followed by the dilator so that the introducer remains positioned at the selected location. The leadless cardiac pacemaker is advanced 688 into the coronary sinus for positioning at the selected location, exposing 690 leadless cardiac pacemaker electrodes. The leadless cardiac pacemaker can be tested 692 at the selected location before retracting 694 the introducer from the patient.

The LCP 100A, 100B, 300A, 300B and/or either catheter system 200, 400 can contain radio-opaque markers for identification under fluoroscopy to aid in positioning.

Terms "substantially", "essentially", or "approximately", that may be used herein, relate to an industry-accepted tolerance to the corresponding term. Such an industry-accepted tolerance ranges from less than one percent to twenty percent and corresponds to, but is not limited to, component values, integrated circuit process variations, temperature variations, rise and fall times, and/or thermal noise. The term "coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. Inferred coupling, for example where one element is coupled to another element by inference, includes direct and indirect coupling between two elements in the same manner as "coupled".

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims. For example, although the description has some focus on pacemakers; systems, structures, and techniques can otherwise be applicable to other uses. Phraseology and terminology employed herein are for the purpose of the description and should not be regarded as limiting. With respect to the description, optimum dimensional relationships for the component parts are to include variations in size, materials, shape, form, function and manner of operation, assembly and use that are deemed readily apparent and obvious to one of ordinary skill in the art and all equivalent relationships to those illustrated in the drawings and described in the specification are intended to be encompassed by the present description. Therefore, the foregoing is considered as illustrative only of the principles of structure and operation. Numerous modifications and changes will readily occur to those of ordinary skill in the art whereby the scope is not limited to the exact construction and operation shown and described, and accordingly, all suitable modifications and equivalents may be included.

What is claimed is:

1. A delivery system configured for implanting a biostimulation device comprising: a stylet comprising a knob end and a threaded end configured to engage a threaded end of the biostimulation device; and a catheter tube configured to axially contain the stylet, the catheter tube comprising a feature configured to engage a corresponding feature on the biostimulation device to provide rotational counter traction when the stylet is rotated relative to the catheter tube for disengagement of the stylet threaded end from the biostimulation device threaded end, wherein the catheter tube further comprises: a sliding sheath assembly configured to axially slide over the stylet and engaged biostimulation device and to axially retract from the stylet a predetermined distance whereby electrodes of the biostimulation device are exposed, enabling threshold testing while the biostimulation device remains engaged to the stylet.

2. The system according to claim 1 further comprising:
   the sliding sheath configured to protect patient tissue from damage during insertion of the biostimulation device.

3. The system according to claim 1 further comprising:
   the sliding sheath assembly further comprising a feature configured to engage and rotate the biostimulation device and affix a fixation member coupled to the biostimulation device into patient tissue.

4. A delivery system configured for implanting a biostimulation device comprising:
   a stylet comprising a knob end and a threaded end configured to engage a threaded end of the biostimulation device; and
   a catheter tube configured to axially contain the stylet, the catheter tube comprising a feature configured to engage a corresponding feature on the biostimulation device to provide rotational counter traction when the stylet is rotated relative to the catheter tube for disengagement of the stylet threaded end from the biostimulation device threaded end, the catheter tube comprising a sheath, the sheath comprising a sheath slot configured to align with an alignment pin of the biostimulation device that prevents rotation of the biostimulation device with respect to the sheath; and
   the stylet configured whereby for the knob fully retracted the biostimulation device is fully contained within the sheath and a fixation member coupled to the biostimulation device is protected, and whereby for the knob fully depressed the alignment pin is contained within the sheath and electrodes of the biostimulation device are fully exposed, enabling threshold testing before disengagement.

5. A delivery apparatus for implanting a leadless cardiac pacemaker comprising: a bi-concentric-axial element catheter comprising an internal stylet element and an externally circumferential tube element, the bi-concentric-axial element catheter configured for engaging to and disengaging from the leadless cardiac pacemaker via relative motion of the internal stylet element to the externally circumferential tube element; and the tube element adapted to engage a corresponding feature on the leadless cardiac pacemaker wherein the stylet element can be rotated relative to the tube element for disengagement of a stylet threaded end from a leadless cardiac pacemaker threaded end, the tube element comprising a sliding sheath configured to axially slide over the stylet and the leadless cardiac pacemaker, the sliding sheath configured to protect patient tissue from damage during insertion of the leadless cardiac pacemaker and to axially retract from the stylet a predetermined distance whereby electrodes of the leadless cardiac pacemaker are exposed, enabling threshold testing while the leadless cardiac pacemaker remains engaged to the stylet, the sliding sheath comprising a feature that engages a corresponding feature on the leadless cardiac pacemaker whereby the stylet can be rotated relative to the sliding sheath for disengagement of the stylet threaded end from the leadless cardiac pacemaker threaded end.

6. A delivery apparatus for implanting a leadless cardiac pacemaker comprising:
   a catheter comprising an internal stylet element and an externally circumferential tube element, the stylet configured for engaging to and disengaging from the leadless cardiac pacemaker via relative motion of the stylet and the tube element;
   the tube element being configured to axially retract from the stylet a predetermined distance whereby electrodes of the leadless cardiac pacemaker are exposed, enabling threshold testing while the leadless cardiac pacemaker remains engaged to the stylet,
   wherein the tube element further comprises a feature adapted to engage a corresponding feature on the leadless cardiac pacemaker to provide rotational counter traction wherein the stylet element can be rotated relative to the tube element for disengagement of the stylet from the leadless cardiac pacemaker.

7. The delivery apparatus of claim 6 wherein the tube element feature is further adapted to rotate the leadless cardiac pacemaker and affix a fixation member of the leadless cardiac pacemaker to patient tissue.

* * * * *